US009233055B2

(12) United States Patent
Glenn, Jr. et al.

(10) Patent No.: US 9,233,055 B2
(45) Date of Patent: Jan. 12, 2016

(54) PERSONAL CARE COMPOSITION IN THE FORM OF A DISSOLVABLE ARTICLE

(71) Applicant: The Procter & Gamble Company, Cincinnati, OH (US)

(72) Inventors: Robert Wayne Glenn, Jr., Cincinnati, OH (US); Eric Paul Granberg, Cincinnati, OH (US); Lynn Kristin Stechschulte, Cincinnati, OH (US); Matthew Steven Ritter, Liberty Township, OH (US); Jason Donald McCarty, Wilmington, OH (US); Michael Edward Thomas, Cincinnati, OH (US); Todd Ryan Thompson, Loveland, OH (US); Jay Ryan Tenkman, Fairfield Township, OH (US); Emily Ragland Muszynski, Cincinnati, OH (US); Dale Francis Bittner, Harrison, OH (US); Nathan Alan Gill, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 14/051,822

(22) Filed: Oct. 11, 2013

(65) Prior Publication Data
US 2014/0105946 A1  Apr. 17, 2014

Related U.S. Application Data

(60) Provisional application No. 61/713,244, filed on Oct. 12, 2012.

(51) Int. Cl.
| | |
|---|---|
| *A61K 8/02* | (2006.01) |
| *A61Q 5/02* | (2006.01) |
| *A61Q 19/00* | (2006.01) |
| *A61Q 19/08* | (2006.01) |
| *A61Q 19/10* | (2006.01) |
| *A61Q 5/12* | (2006.01) |
| *A61K 8/44* | (2006.01) |
| *A61K 8/46* | (2006.01) |
| *A61K 8/81* | (2006.01) |

(52) U.S. Cl.
CPC ............ *A61K 8/0216* (2013.01); *A61K 8/0233* (2013.01); *A61K 8/442* (2013.01); *A61K 8/463* (2013.01); *A61K 8/8129* (2013.01); *A61Q 5/02* (2013.01); *A61Q 5/12* (2013.01); *A61Q 19/00* (2013.01); *A61Q 19/08* (2013.01); *A61Q 19/10* (2013.01)

(58) Field of Classification Search
CPC ....... A61K 8/0216; A61K 8/463; A61K 8/02; A61Q 19/00; A61Q 5/02; A61Q 19/10
USPC ............................... 424/401, 70.11, 400, 642
See application file for complete search history.

(56) References Cited

U.S. PATENT DOCUMENTS

| | | |
|---|---|---|
| 2,356,168 A | 8/1941 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer et al. |
| 2,658,072 A | 11/1953 | Kosmin |
| 2,694,668 A | 11/1954 | Fricke |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau et al. |
| 3,332,880 A | 7/1967 | Kessler |
| 3,426,440 A | 2/1969 | Shen |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz |
| 3,761,418 A | 9/1973 | Parran, Jr. |
| 3,929,678 A | 12/1975 | Laughlin |
| 3,967,921 A | 7/1976 | Haberli |
| 4,020,156 A | 4/1977 | Murray |
| 4,051,081 A | 9/1977 | Jabs et al. |
| 4,089,945 A | 5/1978 | Brinkman |
| 4,149,551 A | 4/1979 | Benjamin et al. |
| 4,196,190 A | 4/1980 | Gehman |
| 4,197,865 A | 4/1980 | Jacquet |

(Continued)

FOREIGN PATENT DOCUMENTS

| | | |
|---|---|---|
| CN | 1138091 | 12/1996 |
| CN | 1219388 A | 6/1999 |

(Continued)

OTHER PUBLICATIONS

ISR dated Jul. 20, 2012, PCT/US2012/032253, 5 pages.
All Office Actions, U.S. Appl. No. 12/424,812.
All Office Actions, U.S. Appl. No. 12/633,257.
All Office Actions, U.S. Appl. No. 12/633,301.
All Office Actions, U.S. Appl. No. 12/633,550.
All Office Actions, U.S. Appl. No. 12/633,335.
All Office Actions, U.S. Appl. No. 12/633,415.
All Office Actions, U.S. Appl. No. 12/633,572.
All Office Actions, U.S. Appl. No. 12/361,634.
All Office Actions, U.S. Appl. No. 12/962,846.
All Office Actions, U.S. Appl. No. 12/962,873.

(Continued)

*Primary Examiner* — Robert A Wax
*Assistant Examiner* — Tracy Liu
(74) *Attorney, Agent, or Firm* — Angela K. Haughey (57) ABSTRACT

An article that is a porous, dissolvable solid structure that dissolves easily due to the shape, product orientation and/or method of manufacturing the porous, dissolvable solid structure. The process of making the Article involves preparing a pre-mixture, aerating the pre-mixture, dosing the pre-mixture into individual cavities in molds, and drying the pre-mixture to an Article having an open celled foam with a % open cell of from about 80% to about 100%.

14 Claims, 3 Drawing Sheets

(56) References Cited

U.S. PATENT DOCUMENTS

| | | |
|---|---|---|
| 4,206,196 A | 6/1980 | Davis |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,663,158 A | 5/1987 | Wolfram |
| 4,710,374 A | 12/1987 | Grollier |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard et al. |
| 5,055,384 A | 10/1991 | Kuhnert |
| 5,061,481 A | 10/1991 | Suzuki |
| 5,062,889 A | 11/1991 | Hohl et al. |
| 5,094,853 A | 3/1992 | Hagarty |
| 5,100,657 A | 3/1992 | Ansher-Jackson |
| 5,100,658 A | 3/1992 | Bolich, Jr. |
| 5,104,646 A | 4/1992 | Bolich, Jr. |
| 5,106,609 A | 4/1992 | Bolich, Jr. |
| 5,166,276 A | 11/1992 | Hayama |
| 5,220,033 A | 6/1993 | Kamei et al. |
| 5,261,426 A | 11/1993 | Kellett et al. |
| 5,280,079 A | 1/1994 | Allen |
| RE34,584 E | 4/1994 | Grote |
| 5,391,368 A | 2/1995 | Gerstein |
| 5,409,703 A | 4/1995 | McAnalley |
| 5,429,628 A | 7/1995 | Trinh |
| 5,457,895 A | 10/1995 | Thompson et al. |
| 5,476,597 A | 12/1995 | Sakata et al. |
| 5,580,481 A | 12/1996 | Sakata et al. |
| 5,582,786 A | 12/1996 | Brunskill |
| 5,660,845 A | 8/1997 | Trinh |
| 5,672,576 A | 9/1997 | Behrens |
| 5,674,478 A | 10/1997 | Dodd |
| 5,750,122 A | 5/1998 | Evans |
| 5,780,047 A | 7/1998 | Kamiya et al. |
| 5,955,419 A | 9/1999 | Barket, Jr. |
| 5,976,454 A | 11/1999 | Sterzel et al. |
| 6,010,719 A | 1/2000 | Remon |
| 6,106,849 A | 8/2000 | Malkan et al. |
| 6,177,391 B1 | 1/2001 | Zafar |
| 6,200,949 B1 | 3/2001 | Reijmer |
| 6,365,142 B1 | 4/2002 | Tamura |
| 6,458,754 B1 | 10/2002 | Velazquez |
| 6,503,521 B1 | 1/2003 | Atis et al. |
| 6,525,034 B2 | 2/2003 | Dalrymple et al. |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Klotzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,943,200 B1 | 9/2005 | Corrand et al. |
| 7,015,181 B2 | 3/2006 | Lambino |
| 7,208,460 B2 | 4/2007 | Shefer et al. |
| 7,285,520 B2 | 10/2007 | Krzysik et al. |
| 7,387,787 B2 | 6/2008 | Fox |
| 7,846,462 B2 | 12/2010 | Spadini et al. |
| 7,901,696 B2 | 3/2011 | Eknoian |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. et al. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn et al. |
| 8,349,787 B2 | 1/2013 | Glenn et al. |
| 8,415,287 B2 | 4/2013 | Glenn, Jr. et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| 8,476,211 B2 | 7/2013 | Glenn, Jr. et al. |
| 8,546,640 B2 | 10/2013 | Popovsky et al. |
| 2002/0064510 A1 | 5/2002 | Dalrymple |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada |
| 2002/0187181 A1 | 12/2002 | Godbey et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan et al. |
| 2003/0099691 A1 | 5/2003 | Lydzinski |
| 2003/0099692 A1 | 5/2003 | Lydzinski et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0053808 A1 | 3/2004 | Raehse et al. |
| 2004/0071742 A1 | 4/2004 | Popplewell |
| 2004/0108615 A1 | 6/2004 | Foley |
| 2004/0110656 A1 | 6/2004 | Casey |
| 2004/0126585 A1 | 7/2004 | Kerins et al. |
| 2004/0175404 A1 | 9/2004 | Shefer |
| 2004/0202632 A1 | 10/2004 | Gott |
| 2004/0206270 A1 | 10/2004 | Vanmaele |
| 2004/0242097 A1 | 12/2004 | Hasenoehrl et al. |
| 2004/0242772 A1 | 12/2004 | Huth et al. |
| 2005/0069575 A1 | 3/2005 | Fox |
| 2005/0136780 A1 | 6/2005 | Clark et al. |
| 2005/0137272 A1 | 6/2005 | Gaserod et al. |
| 2005/0202992 A1 | 9/2005 | Grandio Portabales |
| 2005/0220745 A1 | 10/2005 | Lu |
| 2005/0232954 A1 | 10/2005 | Yoshinari |
| 2005/0272836 A1 | 12/2005 | Yaginuma et al. |
| 2005/0287106 A1 | 12/2005 | Legendre |
| 2006/0002880 A1 | 1/2006 | Peffly |
| 2006/0013869 A1 | 1/2006 | Ignatious et al. |
| 2006/0052263 A1 | 3/2006 | Roreger |
| 2006/0228319 A1 | 10/2006 | Vona, Jr. et al. |
| 2007/0028939 A1 | 2/2007 | Mareri et al. |
| 2007/0149435 A1 | 6/2007 | Koenig |
| 2007/0225388 A1 | 9/2007 | Cooper et al. |
| 2008/0035174 A1 | 2/2008 | Aubrun-Sonneville et al. |
| 2008/0083420 A1 | 4/2008 | Glenn et al. |
| 2008/0090939 A1 | 4/2008 | Netravali et al. |
| 2008/0131695 A1 | 6/2008 | Aouad |
| 2008/0138492 A1 | 6/2008 | Cingotti |
| 2008/0152894 A1 | 6/2008 | Beihoffer |
| 2008/0215023 A1 | 9/2008 | Scavone |
| 2008/0292669 A1 | 11/2008 | Deng et al. |
| 2008/0293839 A1 | 11/2008 | Stobby |
| 2009/0232873 A1 | 9/2009 | Glenn et al. |
| 2010/0167971 A1 | 7/2010 | Glenn, Jr. |
| 2010/0173817 A1 | 7/2010 | Glenn, Jr. |
| 2010/0291165 A1 | 11/2010 | Glenn, Jr. |
| 2010/0298188 A1* | 11/2010 | Glenn et al. .................. 510/120 |
| 2011/0023240 A1 | 2/2011 | Fossum |
| 2011/0027328 A1 | 2/2011 | Baig et al. |
| 2011/0028374 A1 | 2/2011 | Fossum |
| 2011/0182956 A1 | 7/2011 | Glenn, Jr. |
| 2011/0195098 A1 | 8/2011 | Glenn, Jr. |
| 2011/0250256 A1 | 10/2011 | Hyun-Oh et al. |
| 2012/0021026 A1 | 1/2012 | Glenn, Jr. et al. |
| 2012/0270029 A1 | 10/2012 | Glenn, Jr. et al. |

(56) References Cited

U.S. PATENT DOCUMENTS

| | | |
|---|---|---|
| 2012/0321580 A1 | 12/2012 | Glenn, Jr. et al. |
| 2013/0236520 A1 | 9/2013 | Popovsky et al. |

FOREIGN PATENT DOCUMENTS

| | | |
|---|---|---|
| CN | 1268558 A | 10/2000 |
| CN | 1357613 | 7/2002 |
| CN | 1530431 | 9/2004 |
| CN | 1583991 A | 2/2005 |
| DE | 19607851 A1 | 9/1997 |
| DE | 10331767 A1 | 2/2005 |
| EP | 609808 A1 | 8/1994 |
| EP | 0858828 A1 | 8/1998 |
| EP | 1160311 B1 | 12/2001 |
| EP | 1217987 B1 | 12/2004 |
| EP | 1958532 A2 | 8/2008 |
| EP | 2085434 A1 | 8/2009 |
| FR | 2871685 A1 | 12/2005 |
| FR | 2886845 A1 | 12/2006 |
| GB | 2235204 A | 2/1991 |
| GB | 2355008 A | 4/2001 |
| JP | 58021608 | 2/1983 |
| JP | 58216109 | 12/1983 |
| JP | 62-072609 | 4/1987 |
| JP | 62-072610 | 4/1987 |
| JP | 62-081432 | 4/1987 |
| JP | 01313418 | 12/1989 |
| JP | 5344873 A | 12/1993 |
| JP | 6017083 A | 1/1994 |
| JP | 07-53349 | 2/1995 |
| JP | 7089852 A | 4/1995 |
| JP | 08-325133 A | 12/1996 |
| JP | 10251371 A1 | 9/1998 |
| JP | 200373700 A | 3/2003 |
| JP | 200382397 | 3/2003 |
| JP | 2004345983 A | 12/2004 |
| JP | 2005171063 A | 6/2005 |
| JP | 2007197540 A | 8/2007 |
| JP | 2007091954 A | 12/2007 |
| KR | 2002-0003442 | 1/2002 |
| WO | 95/14495 A1 | 6/1995 |
| WO | 01/19948 A1 | 3/2001 |
| WO | 01/24770 A1 | 4/2001 |
| WO | 01/25322 A1 | 4/2001 |
| WO | 01/25393 A1 | 4/2001 |
| WO | 01/54667 A1 | 8/2001 |
| WO | 2004/032859 A | 4/2004 |
| WO | 2004/041991 A1 | 5/2004 |
| WO | 2005/003423 A1 | 1/2005 |
| WO | 2007/033598 A1 | 3/2007 |
| WO | 2007/093558 A1 | 8/2007 |
| WO | 2009/019571 A1 | 2/2009 |

OTHER PUBLICATIONS

All Office Actions, U.S. Appl. No. 12/962,888.
All Office Actions, U.S. Appl. No. 12/962,905.
All Office Actions, U.S. Appl. No. 13/173,639.
All Office Actions, U.S. Appl. No. 13/440,475.
All Office Actions, U.S. Appl. No. 13/597,539.
All Office Actions, U.S. Appl. No. 13/561,298.
ISR dated May 6, 2011, PCT/US2009/067130, 5 pages.
ISR dated May 4, 2011, PCT/US2009/067088, 5 pages.
ISR dated Jul. 19, 2011, PCT/US2009/067088, 7 pages.
ISR dated May 9, 2011, PCT/US2009/067132, 5 pages.
ISR dated Jul. 20, 2011, PCT/US2009/067131, 5 pages.
ISR dated Apr. 29, 2011, PCT/US2009/067089, 5 pages.
ISR dated Jul. 15, 2009, PCT/IB2009/050388, 8 pages.
ISR dated Aug. 17, 2009, PCT/US2009/040739, 6 pages.
ISR dated Nov. 4, 2009, PCT/US2009/040739, 10 pages.
ISR dated Dec. 15, 2011, PCT/US2009/067087, 5 pages.
ISR dated Jul. 19, 2011, PCT/US2009/067133, 4 pages.
ISR dated Jul. 19, 2011, PCT/US2009/067130, 7 pages.
ISR dated Apr. 27, 2011, PCT/US2010/059365, 5 pages.
ISR dated Apr. 27, 2011, PCT/US2010/059455, 5 pages.
ISR dated Apr. 27, 2011, PCT/US2010/059359, 5 pages.
ISR dated Jun. 7, 2013, PCT/US2010/059441, 9 pages.
ISR dated Feb. 20, 2013, PCT/US2011/042640, 12 pages.
C. D. Vaughan. Solubility, Effects in Product, Package, Penetration and Preservation, Cosmetics and Toiletries, vol. 103, Oct. 1988.
Encyclopedia of Polymer Science and Engineering, vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog /ProductDetail.do?D7=0 &N25=SEARCH_CONCAT_PNO%7CBRAND_KEY &N4=P8136%7CSIAL&N25=0&QS=0N& F=SPEC> [retrieved on Jul. 28, 2009].
T. Hildebrand, P. Rüegsegger. Quantification of bone microarchitecture with the structure model index. Comp Meth Biomech Biomed Eng 1997; 1:15-23.
Vesterby,A.; Star vol. In Bone Research a Histomorphometric Analysis of Trabecular Bone Structure Using Vertical Sections; Anat Rec.; Feb. 1993; 235(2):325-334.
PCT International Search Report and Written Opinion for PCT/US2013/064507 dated Nov. 11, 2014.

\* cited by examiner

PERSONAL CARE COMPOSITION IN THE FORM OF A DISSOLVABLE ARTICLE

FIELD OF THE INVENTION

The present invention relates to personal care compositions, especially those personal care compositions in the form of an article that is a porous, dissolvable solid structure. The article dissolves easily due to the shape, product orientation and/or method of manufacturing the porous, dissolvable solid structure.

BACKGROUND OF THE INVENTION

Dissolvable porous solid personal care products have been disclosed, comprising a water-soluble polymeric structurant and a surfactant or other ingredient. However, existing processes for making these dissolvable porous solid structures have less optimal cost, rate of manufacture, and product variability parameters.

A need still exists for a process that results in a desired flexible, dissolvable porous solid structure which can be manufactured within the desired cost and rate parameters. Furthermore, a need exists for a process that results in a dissolvable porous solid structure that dissolves easily. Additionally, it is desirable to improve the dissolving properties of the porous solid personal care product to facilitate improved consumer satisfaction with the product.

SUMMARY OF THE INVENTION

A personal care article in the form of a porous dissolvable solid structure, comprising: from about 0% to about 75% surfactant; from about 15% to about 70% polymeric structurant, wherein the polymeric structurant has a weighted average molecular weight of from about 40,000 to about 500,000; and from about 1% to about 30% plasticizer; wherein the article is an open celled foam with a % open cell of from about 80% to about 100% and, the article has a top and a bottom, and wherein the top comprises an Acquisition Region having pores with an average diameter of from about 0.125 to about 0.850 mm. Additionally, the bottom can have pores having a diameter of from about 0.020 to about 0.125 mm.

A personal care article in the form of a porous dissolvable solid structure, comprising: from about 0% to about 75% surfactant; from about 15% to about 70% polymeric structurant, wherein the polymeric structurant has a weighted average molecular weight of from about 40,000 to about 500,000; and from about 1% to about 30% plasticizer; wherein the article is an open celled foam with a % open cell of from about 80% to about 100% and, wherein the article has a top and a bottom, and wherein the top comprises an Acquisition Region wherein the pores have an average diameter of from about 0.125 to about 0.850 mm and wherein the Article has a concave area located at the Acquisition Region.

A process for preparing an article, comprising the steps of: preparing a pre-mixture comprising from about 1% to about 75% surfactant, from about 0.1% to about 25% polymer, from about 0.1% to about 75% water, and optionally from about 0.1% to about 25% plasticizer, wherein said pre-mixture comprises: a viscosity of from about 1000 cps to about 20,000 cps; and wherein said pre-mixture is heated to a temperature in the range of from about 60° C. to about 90° C.; aerating the pre-mixture by introducing a gas into the pre-mixture to form a wet aerated pre-mixture, wherein said wet aerated pre-mixture comprises: a density of from about 0.15 to about 0.65 g/ml; and a bubble size of from about 5 to about 100 microns; dosing the wet pre-mixture into individual cavities in a mold; and drying the wet pre-mixture by applying energy to the molds to heat the wet pre-mixture and evaporate water wherein the article is an open celled foam with a % open cell of from about 80% to about 100%.

DETAILED DESCRIPTION OF THE INVENTION

Definitions

The flexible porous dissolvable solid structure article may be referred to herein as "the Article" or "the Dissolvable Article". All references are intended to mean the flexible porous dissolvable solid structure article.

As used herein, "flexible" means that the Article meets the distance to maximum force values discussed herein.

As used herein, "dissolvable" means that the Article meets the hand dissolution values discussed herein. The Article has a hand dissolution value of from about 1 to about 30 strokes, in one embodiment from about 2 to about 25 strokes, in another embodiment from about 3 to about 20 strokes, and in still another embodiment from about 4 to about 15 strokes as measured by the Hand Dissolution Method.

As used herein "open celled foam" means a solid, interconnected, polymer-containing matrix that defines a network of spaces or cells that contain a gas, typically a gas such as air, without collapse of the foam structure during the drying process, thereby maintaining the physical strength and cohesiveness of the solid. The interconnectivity of the structure may be described by a Star Volume, a Structure Model Index (SMI) and a Percent Open Cell Content.

As used herein, the articles including "a" and "an" when used in a claim, are understood to mean one or more of what is claimed or described.

As used herein, the terms "include," "includes," and "including," are meant to be non-limiting.

The test methods disclosed in the Test Methods Section of the present application should be used to determine the respective values of the parameters of Applicants' inventions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Figure 1:
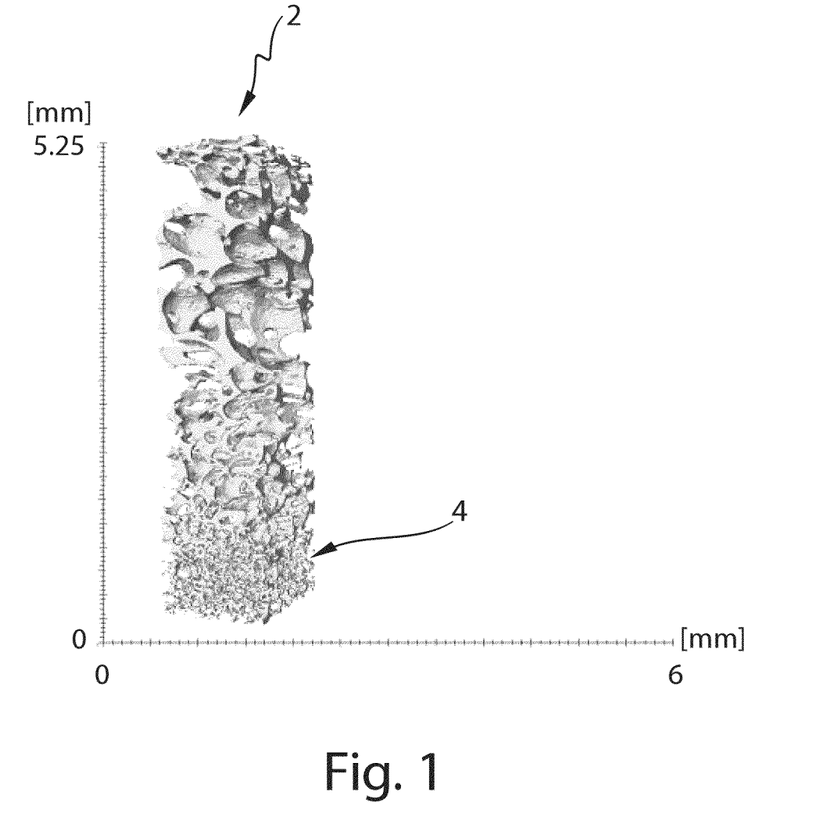
FIG. 1 is a microCT of an Article showing pores.

It has been found that an Article produced according to the molding process as described herein, may form large pores towards the exterior surface of the Article. The Articles have a top and a bottom. These larger pores may be on one side of the Article only, and may be only on the portion of the Article which contacts the mold. The portion of the Article which contacts the mold during manufacture, becomes the top of the Article during use. The top portion of the Article which has large pores can be considered the Acquisition Region, as this Region is more receptive to water. The pores on the Acquisition Region can have a diameter from about 0.125 to about 0.850 mm. The bottom portion of the Article may have smaller pores, from a diameter of about 0.020 to about 0.125 mm, and as such is less receptive to water. These areas of smaller pore size can be considered the Non-Acquisition Region, as they are less receptive to water. It has been found that the dissolution of the Article can be improved if water is added first to the Acquisition Region of the Article. FIG. 1 shows a microcomputed tomography (mCT) image of an Article, having an Acquisition Region 2, and Non-Acquisition Region 4.

In one example the hand dissolution test indicates that the dissolution of the Article where water is first added to the Acquisition Region dissolves easier and more completely into a liquid product (see Table 1 vs. Table 2).

TABLE 1

Water Added to Acquisition Region First

| Article Weight | Dissolution (hand dissolution method) |
|---|---|
| 1.6275 | 6 |
| 1.8091 | 6 |

TABLE 2

Water Added to Non-Acquisition Region First

| Article Weight | Dissolution (hand dissolution method) |
|---|---|
| 1.8126 | 30+ |
| 1.8360 | 30+ |

Figure 2:
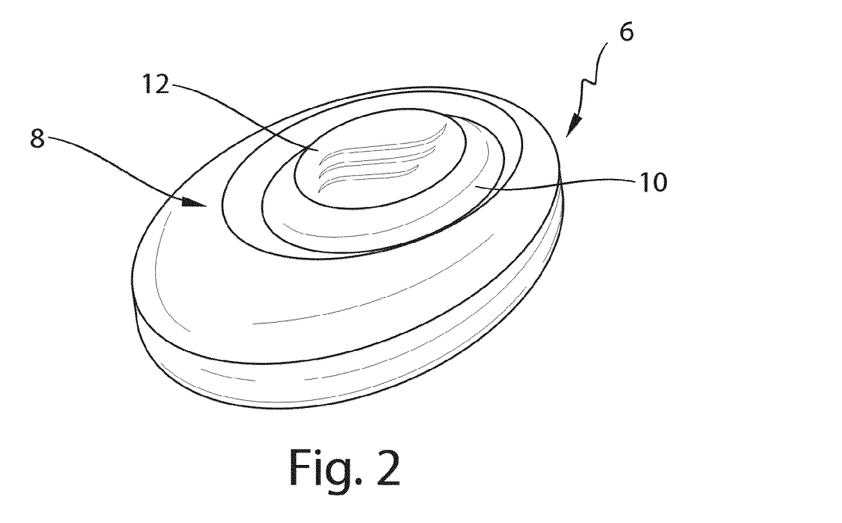
FIG. 2 is a top view of an embodiment of an Article.
Figure 3:
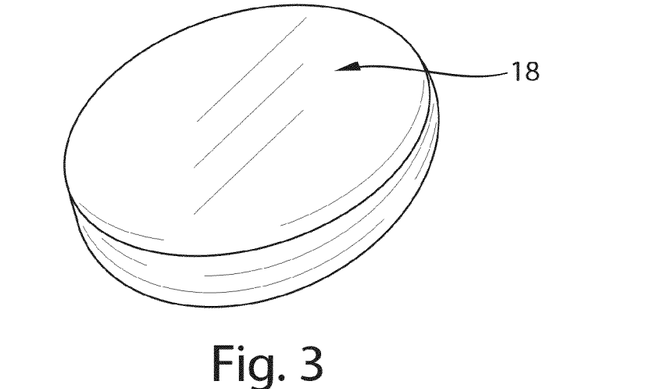
FIG. 3 is a bottom view of an embodiment of an Article.
Figure 4:
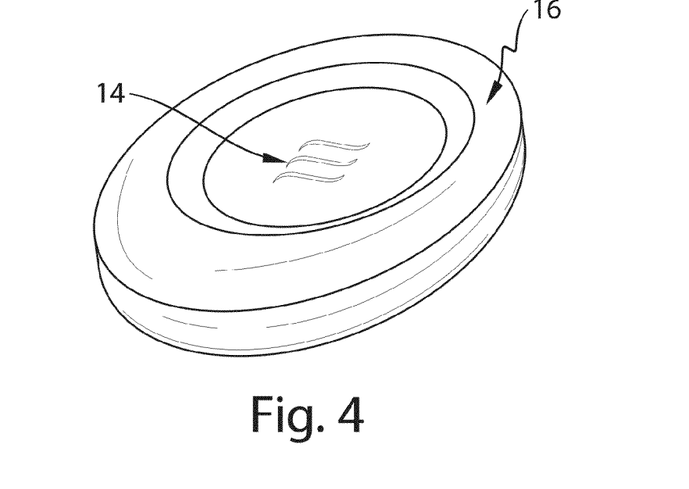
FIG. 4 is a top view of an embodiment of an Article.

An embodiment of the Article is shown in FIGS. 2 and 3. This Article has a top side (FIG. 2) and a bottom side (FIG. 3). In manufacture, the top side of the Article is the portion of the Article which contacts the mold. An indicia and/or logo can be used to encourage the consumer to add water to the Acquisition Region of the Article 6 (as shown in FIG. 2). Another way of improving the dissolution of the Article is for the Acquisition Region 8 of the Article to also be shaped to receive and/or hold water (FIG. 2). This shaping can be achieved via channels, 10 or a logo which includes grooves 12. The Article may also be shaped such that the Acquisition Region has a depression and/or concave area 14 where water can be received (As shown in FIG. 4). This further encourages the consumer to add water to the Acquisition Region of the Article, and as such increases the ease of dissolution of the Article.

Figure 5:
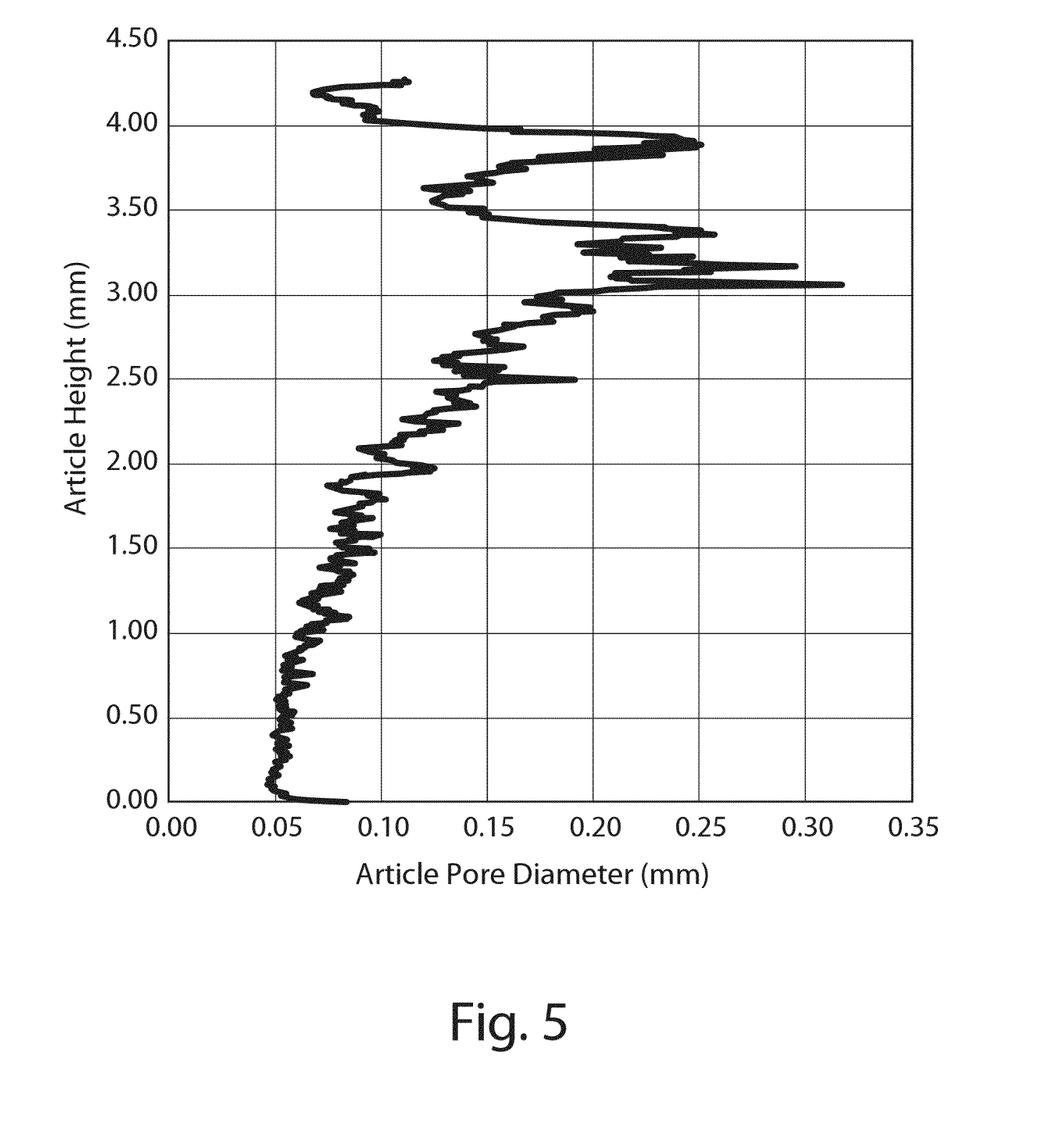
FIG. 5 is a graph showing Article pore diameter in mm vs. Article height in mm.

As shown in FIG. 5, the diameter of the pores—which is determine by taking the weighted radius (method described herein) value at each slice and multiplying by two. The diameter of the pores are larger in one region of the Article.

The molding process facilitates this shaping of the Article, as any manner of combination of shapes, grooves, impressions, and/or indicia can be formed into the Article during the molding process. The Article takes on whatever shape is included in the mold. The Non-Acquisition Region can be generally flat 12 (as shown in FIG. 3). Additionally, the Non-Acquisition Region can be molded or shaped to indicate that it should be placed in the palm of the consumer. This can be a convex region that could fit into the consumers hand more easily than a flat surface. This further serves as an indicator for the consumer to apply water to the Acquisition Region of the Article.

Additionally, the Article can include indicia which allows the consumer to locate the top and bottom of the product, and therefore know where to add water. The indicia includes, but is not limited to colors, designs, textures, shapes, particulates, printed letters (such as top, bottom etc). These indicia can be included on the article in any manner, including but not limited to formed into the Article, molded into the Article, printed on the Article and/or sprayed onto the Article.

It has further been found that the molding process can be utilized to make Articles which have a center thickness that is thinner relative to the edge. This increased area foot print helps reduce the overall thickness of the pad. This Article can be dried faster. During the drying process heat can be added from the top, bottom and sides, which encourages evaporation of water. If the Articles dry faster, the Articles can be manufactured faster and/or more economically. As shown in FIG. 4, the center region 14 can be thinner than the outer regions 16 of the Article.

Method of Manufacture

A. Preparation of Pre-Mixture

The pre-mixture is generally prepared by mixing the solids of interest, including surfactant(s), dissolved water soluble polymer, optional plasticizer and other optional ingredients. In one embodiment, the solids of interest are present in the pre-mixture at a level by weight of from about 1% to about 75% surfactant, from about 0.1% to about 25% water soluble polymer, and from about 0.1% to about 25% plasticizer.

In one embodiment, the pre-mixture can be formed using a mechanical mixer. Mechanical mixers useful herein, include, but aren't limited to pitched blade turbines or MAXBLEND mixer (Sumitomo Heavy Industries).

For addition of the ingredients in the pre-mixture, it can be envisioned that the polymer is ultimately dissolved in the presence of water, the surfactant(s), optional actives, optional plasticizer, and any other optional ingredients including stepwise processing via pre-mix portions of any combination of ingredients.

The pre-mixtures of the present invention comprise: from about 15% to about 55% solids, in one embodiment from about 30% to about 55% solids, in one embodiment from about 32% to about 55% solids, in one embodiment from about 34% to about 50%, and in another embodiment from about 36% to about 45% solids, by weight of the pre-mixture before drying. The percent solids content is the summation of the weight percentages by weight of the total processing mixture of all of the solid, semi-solid and liquid components excluding water and any obviously volatile materials such as low boiling alcohols.

In one embodiment, the viscosity of the pre-mixture is determined when the pre-mixture is heated to a temperature in the range of from about 60° C. to about 99° C. In one embodiment, the viscosity is measured at 1 $sec^{-1}$ and 70° C. In another embodiment, the viscosity of the pre-mixture is measured at ambient temperatures (25° C.).

When the pre-mixture is heated to a temperature in the range of between 60° C. and 99° C., the pre-mixtures of the present invention have a viscosity of from about 1000 cps to about 20,000 cps, in one embodiment from about 2,000 cps to about 15,000 cps, in one embodiment from about 3,000 cps to about 10,000 cps, and in another embodiment from about 4,000 cps to about 7,500 cps. The pre-mixture viscosity values are measured using a Brookfield RVDV-1 Prime Viscometer with CPE-41 cone and a shear rate of 1.0 reciprocal seconds for a period of 300 seconds.

B. Optional Continued Heating of Pre-Mixture

Optionally, the pre-mixture is pre-heated immediately prior to the aeration process at above ambient temperature but below any temperatures that would cause degradation of the components. In one embodiment, the pre-mixture is kept at above about 40° C. and below about 99° C., in another embodiment above about 50° C. and below about 95° C., in another embodiment from about 60° C. and below about 90° C. In one embodiment, when the pre-mixture is heated to a temperature in the range of between 60° C. and 99° C., the pre-mixtures of the present invention have a viscosity of from about 1000 cps to about 20,000 cps, in one embodiment from about 2,000 cps to about 15,000 cps, in one embodiment from about 3,000 cps to about 10,000 cps, and in another embodiment from about 4,000 cps to about 7,500 cps. In an additional embodiment, additional heat is applied during the aeration process to try and maintain an elevated temperature during the aeration. This can be accomplished via conductive heating from one or more surfaces, injection of steam or other processing means.

It is believed that the act of pre-heating the pre-mixture before the aeration step may provide a means for lowering the viscosity of pre-mixtures comprising higher percent solids content for improved introduction of bubbles into the mixture and formation of the desired Article. Achieving higher percent solids content is desirable so as to reduce the energy requirements for drying. The increase of percent solids, and therefore conversely the decrease in water level content, and increase in viscosity is believed to affect the film drainage within the pre-mixture during the drying step. This film drainage and evaporation of water from the pre-mixture during drying is believed to assist the formation of the open celled structure of the Article.

Pre-heating of the pre-mixture also allows for the manufacture of a fast dissolving Article even when using a more viscous processing mixture. Without pre-heating, these viscous processing mixtures with higher percent solid levels normally produce Articles that are slow dissolving and that have predominately closed celled foams. However, the increased temperature during pre-heating causes drainage from the thin liquid film separating the bubbles outwards into the plateau borders of the open celled foam. This drainage generates openings between the bubbles which become the open cells of the Article. The demonstrated ability to achieve such inter-connected open-celled foams of the Articles of the present invention is surprising.

In addition, a more viscous processing mixture results in Articles with low percent (%) shrinkage after the drying process while still maintaining fast dissolution rates. This is due to the fact that during the drying process, pre-mixtures with higher viscosities are able to mitigate the drainage and bubble rupture/collapse/coalescence that give rise to the shrinkage.

C. Aeration of Pre-Mixture

The aeration of the pre-mixture is accomplished by introducing a gas into the pre-mixture in one embodiment by mechanical mixing energy but also may be achieved via chemical means to form an aerated mixture. The aeration may be accomplished by any suitable mechanical processing means, including but not limited to: (i) batch tank aeration via mechanical mixing including planetary mixers or other suitable mixing vessels, or (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In another embodiment, aeration with chemical foaming agents by in-situ gas formation (via chemical reaction of one or more ingredients, including formation of carbon dioxide ($CO_2$ (g)) by an effervescent system) can be used.

In a particular embodiment, it has been discovered that the Article can be prepared within continuous pressurized aerators that are conventionally utilized in the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), the Mondo (Haas-Mondomix B.V., Netherlands), the Aeros (Aeros Industrial Equipment Co., Ltd., Guangdong Province, China), and the Preswhip (Hosokawa Micron Group, Osaka, Japan). Continuous mixers may work to homogenize or aerate slurry to produce highly uniform and stable foam structures with uniform bubble sizes. The unique design of the high shear rotor/stator mixing head may lead to uniform bubble sizes across the thickness of the initially wet aerated pre-mixture that is used to form the Article (prior to drying).

Bubble size of the wet aerated pre-mixture assists in achieving uniformity in the Article. In one embodiment, the bubble size of the wet aerated pre-mixture is from about 5 to about 100 microns and another embodiment, the bubble size is from about 20 microns to about 80 microns.

The uniformity of the bubble sizes causes the Article to have consistent densities in the layers of the Article. In one embodiment, the wet aerated pre-mixture has a density from about 0.15 to about 0.50 g/mol., in one embodiment from about 0.20 to about 0.45 g/mol, in one embodiment from about 0.25 to about 0.40 g/mol, and in another embodiment from about 0.27 to about 0.38 g/mol.

D. Dosing

The wet pre-mixture is then dosed using a manifold-type devise into individual cavities in a mold. Accurate dosing is needed to prevent over- or under-filling of the cavities. Ideally, the top surface will "self-level" and create a smooth, flat surface in the finished Articles; alternatively, scraping can be used to create a smooth, flat surface. Dosing can be performed with commercially available equipment that has been customized to deliver specific shapes and sizes. Suitable equipment can be provided by the E. T. Oakes Corporation, Hauppauge, N.Y., OKA-Spezialmaschinefabrik, Darmstadt, Germany, and Peerless Food Equipment, Sidney, Ohio. Product is dosed into molds that provide the desired shape and design for the finished Article. Molds can be made from a variety of materials including metals, plastics, and composite materials. The use of flexible molds can assist with removal of the finished Article from the molds after drying.

E. Drying

Energy is applied to the wet foam molds to heat the foam and evaporate water. This energy can come from a variety of sources such as hot air, infra-red, radiative heat, etc. As the foam heats up, the air bubbles grow and start pressing against one another. This creates a pressure in the thin films of premix that separate the air bubbles, causing these films to drain into the plateau border regions of the cellular structure. The drying rate and premix rheology is controlled to enable this film drainage, which in turn leads to the formation of an open celled foam structure during drying. This open celled foam structure provides good dissolution in the finished dry foam. If the drying rate and film rheology are not properly matched, the resulting structure may be a closed or partially closed cell foam which does not dissolve well. Drying can be performed using a variety of commercially available equipment, for example, impingement air dryer manufactured by Lincoln (a division of Manitowoc Foodservices) and Autobake Ovens and Baking Systems (Sydney™, Australia). Drying via this method may result in a gradient of open cells pore sizes. The heat applied to the mold may result in uneven heating of the substrate, thus a pore gradient, with the largest pores forming on the side of the foam which is in contact with the mold.

D. Conditioning

Under some drying conditions, there is an internal moisture gradient within the Articles when they exit the dryer. If this gradient is too large, and the center of the Articles are too wet, the quality of the Articles can be compromised in the Article removal step. The Articles may be held for a period of time at controlled temperature and humidity conditions to allow the moisture gradient to equilibrate within the Articles.

E. Removal from Molds

A combination of mold inversion and suction can be used to remove Articles from the molds. Mold inversion is desirable because the porosity of the dried Articles is relatively high and can allow vacuum to pass through the Articles.

F. Minors Addition

Additional minor ingredients may be added to the Articles post-drying—in particular temperature sensitive materials such as perfume that might not withstand the drying conditions. These minors are added in a way that accurately doses the appropriate amount of material onto each Article and provides an acceptable appearance on the finished Article. Suitable methods include spray coating, roll coating and other coating technologies.

G. Article Processing

The Articles can be additionally processed to help with dissolution, specifically holes and/or voids can be added to the exterior portion of the article. In one embodiment holes are burned into the Article (in order to remove a portion of the foam material to create holes and/or voids). In another embodiment holes are poked in the surface of the Article using a needle-like device.

Composition of Article

A. Surfactants

The Article comprises one or more surfactants suitable for application to the hair or skin. Surfactants suitable for use in the Article include anionic surfactants, nonionic surfactants, cationic surfactants, zwitterionic surfactants, amphoteric surfactants, polymeric surfactants or combinations thereof. Various surfactants for use in the Article are set forth in U.S. application Ser. No. 12/633,228. Each patent described throughout this application is incorporated herein by reference to the extent each provides guidance regarding surfactants suitable for inclusion in the Article.

In one embodiment, the premixture comprises from about 1% to about 75% by weight of the Article of surfactant.

In another embodiment, the Article is a lathering dissolvable solid personal care product (dried) and comprises from about 0% to about 75% by weight of the Article of surfactant, in one embodiment from about 23% to about 75% by weight of the Article of surfactant, in one embodiment from about 30% to about 70% by weight of the Article of surfactant, in one embodiment from about 40% to about 65% by weight of the Article of surfactant. In such cases, the pre-mixture may comprise from about 8% to about 30% by weight of the pre-mixture of surfactant, in one embodiment from about 13% to about 28% by weight of the pre-mixture of surfactant, in one embodiment from about 18% to about 25% by weight of the pre-mixture of surfactant.

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glyceryl ether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Anionic surfactants for use in the Article include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. The family of amphoacetates derived from the reaction of sodium chloroacetate with amidoamines to produce alkanoyl amphoacetates are particularly effective, e.g. lauryolamphoacetate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl)sulfopropyl betaine and mixtures thereof. Also suitable amphoteric surfactants include amidobetaines and amidosulfobetaines, wherein the $RCONH(CH_2)_3$ radical is attached to the nitrogen atom of the betaine are also useful herein.

Cationic surfactants may include a DEQA compound. The DEQA compounds encompass a description of diamido actives as well as actives with mixed amido and ester linkages. DEQA compounds are typically made by reacting alkanolamines such as MDEA (methyldiethanolamine) and TEA (triethanolamine) with fatty acids. Some materials that typically result from such reactions include N,N-di(acyl-oxy-ethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids (See U.S. Pat. No. 5,759,990 at column 4, lines 45-66). Additional non-limiting examples of such DEQA compounds are described in U.S. Pat. No. 5,580,481 and U.S. Pat. No. 5,476,597.

Other suitable actives for use as a cationic surfactant include reaction products of fatty acids with dialkylenetriamines in, e.g., a molecular ratio of about 2:1, said reaction products containing compounds of the formula:

wherein $R^1$, $R^2$ are defined as above, and each $R^3$ is a $C_{1-6}$ alkylene group, more specifically an ethylene group. Examples of these actives are reaction products of tallow acid, canola acid, or oleic acids with diethylenetriamine in a molecular ratio of about 2:1, said reaction product mixture containing N,N"-ditallowoyldiethylenetriamine, N,N"-dicanola-oyldiethylenetriamine, or N,N"-dioleoyldiethylenetriamine, respectively, with the formula:

$$R^1—C(O)—NH—CH_2CH_2—NH—CH_2CH_2—NH—C(O)—R^1$$

wherein $R^2$ and $R^3$ are divalent ethylene groups, $R^1$ is defined above and an acceptable examples of this structure when $R^1$ is the oleoyl group of a commercially available oleic acid derived from a vegetable or animal source, include EMERSOL® 223LL or EMERSOL® 7021, available from Henkel Corporation.

Another active for use as a cationic surfactant has the formula:

wherein R, $R^1$, $R^2$, $R^3$ and $X^-$ are defined as above. Examples of this active are the di-fatty amidoamines based softener having the formula:

$$[R^1—C(O)—NH—CH_2CH_2—N(CH_3)\\(CH_2CH_2OH)—CH_2CH_2—NH—C(O)—R^1]^+\\CH_3SO_4^-$$

wherein $R^1$—C(O) is an oleoyl group, soft tallow group, or a hardened tallow group available commercially from Degussa under the trade names VARISOFT® 222LT, VARISOFT® 222, and VARISOFT® 110, respectively.

A second type of DEQA ("DEQA (2)") compound suitable as an active for use as a cationic surfactant has the general formula:

wherein each Y, R, $R^1$, and $X^-$ have the same meanings as before.

These types of agents and general methods of making them are disclosed in U.S. Pat. No. 4,137,180, Naik et al., issued Jan. 30, 1979. An example of a DEQA (2) is the "propyl" ester quaternary ammonium fabric softener active having the formula 1,2-di(acyloxy)-3-trimethylammoniopropane chloride.

Other suitable cationic surfactants can include asymmetric dialkyl quaternized ammonium salt cationic surfactant. The asymmetric dialkyl quaternized ammonium salt cationic surfactant can be included in the composition at a level by weight of in one embodiment from about 0.1% to about 10%, in another embodiment from about 0.2% to about 5%, in yet another embodiment from about 0.4% to about 3% in view of balance between ease-to-rinse feel and wet conditioning benefits. The use of higher level of asymmetric dialkyl quaternized ammonium salt tends to lead to reduced wet conditioning benefits such as reduced slippery feel, while the use of lower level of asymmetric dialkyl quaternized ammonium salt tends to lead to reduced ease-to-rinse feel. Exemplary cationic surfactants and nonionic agents are set forth in U.S. Ser. No. 12/763,286, which is incorporated herein by reference.

In another embodiment, the Article is a substantially non-lathering dissolvable solid personal care product and comprises from about 0% to about 10% by weight of the Article of an ionic (anionic, zwitterionic, cationic and mixtures thereof) surfactant, in one embodiment from about 0% to about 5% by weight of the Article of an ionic surfactant, and in one embodiment from about 0% to about 2.5% by weight of the Article of an ionic surfactant, and from about 1% to about 50% by weight of the Article of a nonionic or polymeric surfactant, in one embodiment from about 5% to about 45% by weight of the Article of a nonionic or polymeric surfactant, and in one embodiment from about 10% to about 40% by weight of the Article of a nonionic or polymeric surfactant, and combinations thereof.

Suitable nonionic surfactants for use in the present invention include those described in McCutcheon's Detergents and Emulsifiers, North American edition (2010), Allured Publishing Corp., and McCutcheon's Functional Materials, North American edition (2010). Suitable nonionic surfactants for use in the Article of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

In another embodiment, the nonionic surfactant selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

Suitable polymeric surfactants include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

B. Polymer

The one or more polymers suitable for the Article herein are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

The polymer(s) of the Article can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrolidone/vinyl acetate copolymers, copolymers of anionic, cationic and amphoteric monomers, and combinations thereof.

The polymer(s) of the Article may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as polymer(s) in the Article. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Water-soluble polymers of the Article include polyvinyl alcohols, polyvinylpyrrolidones, polyalkylene oxides, starch and starch derivatives, pullulan, gelatin, hydroxypropylmethylcelluloses, methylcelluloses, and carboxymethycelluloses.

Water-soluble polymers of the Article also include polyvinyl alcohols, and hydroxypropylmethylcelluloses. Suitable polyvinyl alcohols include those available from Celanese Corporation (Dallas, Tex.) under the CELVOL trade name including, but not limited to, CELVOL 523, CELVOL 530, CELVOL 540, CELVOL 518, CELVOL 513, CELVOL 508, CELVOL 504, and combinations thereof. Suitable hydroxypropylmethylcelluloses include those available from the Dow Chemical Company (Midland, Mich.) under the METHOCEL trade name including, but not limited, to METHOCEL E50, METHOCEL E15, METHOCEL E6, METHOCEL E5, METHOCEL E3, METHOCEL F50, METHOCEL K100, METHOCEL K3, METHOCEL A400, and combinations thereof including combinations with above mentioned hydroxypropylmethylcelluloses.

The Article (dried) may comprise from about 10% to about 50% by weight of the Article of a polymer, in one embodiment from about 15% to about 40% by weight of the Article of polymer, in one embodiment from about 20% to about 30% by weight of the Article of a polymer.

The pre-mixture may comprise from about 0.1% to about 25% by weight of the pre-mixture of polymer, in one embodiment from about 5% to about 15% by weight of the pre-mixture of polymer, in one embodiment from about 7% to about 10% by weight of the pre-mixture of polymer.

C. Plasticizer

The Article may comprise a water soluble plasticizing agent suitable for use in compositions discussed herein. Non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

Plasticizers include glycerin and propylene glycol. EP 0283165 B1 discloses other suitable plasticizers, including glycerol derivatives such as propoxylated glycerol.

The pre-mixture may comprise from about 0.1% to about 25% by weight of the pre-mixture of plasticizer, in one embodiment from 1 to 15% by weight of the pre-mixture of plasticizer, in one embodiment from about 2% to about 10% by weight of the pre-mixture of plasticizer, in one embodiment from about 2% to about 4% by weight of the pre-mixture of plasticizer.

The Article (dried) may comprise from about 1% to about 25% by weight of the Article of plasticizer, in one embodiment from about 3% to about 20% by weight of the Article of plasticizer, in one embodiment from about 5% to about 15% by weight of the Article of plasticizer.

D. Optional Ingredients

The Article may further comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Suitable conditioning agents include high melting point fatty compounds, silicone conditioning agents and cationic conditioning polymers. Suitable materials are discussed in US 2008/0019935, US 2008/0242584 and US 2006/0217288.

Non-limiting examples of product type embodiments for use by the Article include hand cleansing substrates, hair shampoo or other hair treatment substrates, body cleansing substrates, shaving preparation substrates, fabric care substrate (softening), dish cleaning substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Test Methods

A. Distance to Maximum Force Method:

Measured via a Rupture Method on a Texture Analyzer using a TA-57R cylindrical probe with Texture Exponent 32 Software. The Article should have a thickness of between 4 to 7 mm and cut in a circle with a diameter of at least 7 mm for this method; or carefully cut or stacked to be within this overall thickness and diameter range. The porous solid sample is carefully mounted on top of the cylinder with four screws mounted on top with the top lid affixed in place on top of the sample. There is a hole in the center of the cylinder and its lid which allows the probe to pass through and stretch the sample. The sample is measured with a pre-test speed of 1 mm per second, a test speed of 2 mm per second and a post test speed of 3 mm per second over a total distance of 30 mm. The distance to maximum force is recorded.

B. Hand Dissolution Method:

One Article, with dimensions of approximately 43 mm×43 mm×4-6 mm, is placed in the palm of the hand while wearing nitrile gloves. 7.5 cm$^3$ of from about 30° C. to about 35° C. tap water is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum.

C. Lather Profile: Lather Volume:

The Article provides a lather profile as described hereafter. The lather volume assessment is performed on 15 g/10 inch flat Oriental virgin hair switches that have been treated with 0.098 g of artificial liquid sebum [10-22% olive oil, 18-20% coconut oil, 18-20% oleic acid, 5-9% lanolin, 5-9% squalene, 3-6% palmitic acid, 3-6% paraffin oil, 3-6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 cm$^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 ml, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the Article, 0.20+/−0.01 grams of product are weighed with the aid of scissors if required and applied to the switch and then 2 cm$^3$ of additional water are added to the product via syringe. The lathering technique is then performed as described for liquid products after a 10 second waiting time.

As used herein, the terms "substantially non-lathering" and "non-lathering" are used to mean a lather volume of from 0 ml to 20 ml.

D. Cell Wall Thickness/Pore Size

The Article has a maximum Cell Wall Thickness. The Article has a Cell Wall Thickness of from about 15 microns to about 55 microns, in another embodiment from about 20 microns to about 45 microns, and in another embodiment from about 25 microns to about 35 microns.

The Cell Wall Thickness is computed from the scanned images via a micro computed tomography system (µCT80, SN 06071200, Scanco Medical AG) as described herein. The Cell Wall Thickness is determined according to the method defined for the measurement of Trabecular Thickness using Scanco Medical's Bone Trabecular Morphometry evaluation.

The Cell wall thickness and spacing is calculated as the trabecular thickness and trabecular spacing using the ImageJ program with BoneJ plugin. ImageJ is a public domain, Java-based image-processing program developed at the National Institutes of Health and is available for download at http://rsb.info.nih.gov/ij. Information on the development of BoneJ can be found in the following article: Doube M, Klosowski M M, Arganda-Carreras I, Cordelières F, Dougherty R P, Jackson J, Schmid B, Hutchinson J R, Shefelbine S J. (2010) BoneJ: free and extensible bone image analysis in ImageJ. *Bone* 47:1076-9. doi: 10.1016/j.bone.2010.08.023.

BoneJ is an open source/free software plugin for ImageJ to facilitate calculations commonly used in trabecular bone analysis. Images obtained from the Scanco µCT50 have a pixel size equal to 0.002 mm. These images are subsampled to 0.004 mm sized pixels for easier data handling and prepared as a series of binary images (slices) using the program, Aviso Standard v6.3.1. Once the binary images are created, they are exported as a series of 2D TIFF images. The images are then loaded into ImageJ using the "Import Image Sequence" function. They are then analyzed using the BoneJ "Thickness" measurement option. The resulting data has units of pixels and are converted to millimeters by multiplying each data by 0.004.

Weighted Radius can be used to measure the pore diameter. The weighted radius is calculated from the three dimensional data from the mCT. The mCT can be treated as a stack of two dimensional images in the height direction. Estimating the change in bubble diameter from slice to slice is done using the following steps. Each image (or slice) is converted to a binary image by using an appropriate threshold which separates formula material from void space.

Each slice is 3.8 microns. The Article is assigned the bright foreground pixels (value of one) and void space is dark background pixels (value of zero). For each binary slice, the Euclidean distance transform is calculated. The Euclidean distance transform assigns each dark pixel a new value based on the distance to the nearest foreground pixel. Most image processing packages, such as MATLAB, offer the Euclidean distance transform as a standard image processing method. The algorithm can be designed to execute very quickly. The average of the assigned Euclidean distance values multiplied by 3 is used as a surrogate for void bubble diameter and plotted with respect to height (this value is the weighted radius). This weighted radius is then multipled by two to arrive at the pore diameter. (See FIG. 5 for a graph of Article Pore Diameter in mm vs. Article height in mm.) This method is further described in the article Maurer, Calvin, Rensheng Qi, and Vijay Raghavan, "A Linear Time Algorithm for Computing Exact Euclidean Distance Transforms of Binary Images in Arbitrary Dimensions," IEEE Transactions on Pattern Analysis and Machine Intelligence, Vol. 25, No. 2, February 2003, pp. 265-270.

E. Specific Surface Area

The Article also has a minimum Specific Surface Area. The Article has a Specific Surface Area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$.

The Specific Surface Area is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

F. Thickness

In one embodiment the Article is a flat, flexible substrate in the form of a pad (including but not limited to pads formed in a molding process), a strip, or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In another embodiment, the Article is a sheet having a thickness from about 5 mm to about 6.5 mm. In another embodiment, two or more sheets are combined to form an Article with a thickness of about 5 mm to about 10 mm. If the pad has a concave dimension, the center of the pad 14 can be about 1 to about 2 mm thinner than the perimeter 16. (See FIG. 4) In one embodiment the perimeter of the pad is about 7 to about 8 mm, and the center of the pad is from about 5 to about 6.5 mm.

The thickness of the dissolvable porous solid (i.e., substrate or sample substrate) can be obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). Alternately, the thickness can be measured by cutting the pad in a cross section and directly measuring the thick and thin sections with a measuring rule, or via optical microscopy imaging and/or measurement.

G. Basis Weight

The Article has a basis weight of from about 200 grams/$m^2$ to about 2,000 grams/$m^2$, in one embodiment from about 400 grams/$m^2$ to about 1,200 grams/$m^2$, in another embodiment from about 600 grams/$m^2$ to about 2,000 grams/$m^2$, and in still another embodiment from about 700 grams/$m^2$ to about 1,500 grams/$m^2$.

The Basis Weight of the dissolvable porous solid component of the personal care composition herein is calculated as the weight of the dissolvable porous solid component per area of the selected dissolvable porous solid (grams/$m^2$). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as 3.14×(diameter/2)$^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

H. Dry Density

The Article has a dry density of from about 0.08 g/$cm^3$ to about 0.30 g/$cm^3$, in one embodiment from about 0.10 g/$cm^3$ to about 0.25 g/$cm^3$, and in another embodiment from about 0.12 g/$cm^3$ to about 0.20 g/$cm^3$.

The dry density of the dissolvable porous solid is determined by the equation: Calculated Density=Basis Weight of porous solid/(Porous Solid Thickness×1,000). The Basis Weight and Thickness of the dissolvable porous solid are determined in accordance with the methodologies described herein.

I. Scanning Electron Microscope (SEM) Imaging

Representative sections were cut from the sponge with a clean razor blade and mounted with the cut face up on a standard cryo-SEM stub. Samples were secured onto the stub with carbon tape and silver paint. Samples were imaged using an Hitachi S-4700 FE-SEM fitted with a Gatan Alto 2500 cryo stage. Samples were cooled to −95 dC before imaging in the microscope. Samples were lightly coated with Platinum to reduce charging. Representative images were collected at 2 kV, 20 uA extraction voltage, ultra high resolution mode using the lower secondary electron detector. Long working distances were used to allow the entire sample to be imaged in one frame.

J. Star Volume and Structure Model Index

The Article has a Star Volume of from about 1 mm$^3$ to about 90 mm$^3$, in one embodiment from about 5 mm$^3$ to about 80 mm$^3$, in another embodiment from about 10 mm$^3$ to about 70 mm$^3$, and in still another embodiment from about 15 mm$^3$ to about 60 mm$^3$. The Article has a non-negative Structure Model Index of from about 0.0 to about 3.0, in one embodiment from about 0.5 to about 2.75, and in another embodiment from about 1.0 to about 2.50.

To measure the cell interconnectivity via the Star Volume and the Structure Model Index, disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, Star Volume measurements are made. Star Volume is a measure of the "openness" of the void space in a two phase structure. By choosing a random uniformly distributed set of points in the phase of interest (in this case the phase of interest is the void space or air), lines can be extended in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (only accept lines that actually intersect with the foreground phase). The final equation is based upon the research entitled *Star Volume In Bone Research A Histomorphometric Analysis Of Trabecular Bone Structure Using Vertical Sections*; Vesterby, A.; Anat Rec.; 1993 February; 235(2):325-334:

$$StarVolume = \frac{4}{3}\pi \cdot \frac{\sum dist^3}{N}$$

where "dist" is the individual distances and N is the number of lines examined.

K. Open Cell Content

The Article has a Percent Open Cell Content of from about 80% to 100%, in one embodiment from about 85% to about 97.5%, and in another embodiment from about 90% to about 95%.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample of the Article is sealed in the instrument compartment of known volume, the appropriate inert gas is admitted, and then expanded into another precision internal volume. The pressure before and after expansion is measured and used to compute the sample Article volume. Dividing this volume into the sample Article weight gives the gas displacement density.

EXAMPLES

Composition of the Article

| Component | Ex. 1 |
| --- | --- |
| Glycerin | 3.24% |
| Mackam HPL-28ULS Sodium Lauroamphoacetate (22% activity) | 37.05% |
| Sodium Laureth-1-sulfate (70% activity) | 15.71% |
| Sodium Laureth-3-sulfate (28% activity) | 5.36% |
| Celvol 523 | 8.08% |
| Jaguar C500 | 0.50% |
| Citric Acid | 1.50% |
| Distilled water | 28.56% |
| Total | 100 |

Note that any actives and/or compositions disclosed herein can be used in and/or with the Articles, disclosed in the following U.S. Patent Applications, including any publications claiming priority thereto: U.S. 61/229,981; U.S. 61/229,986; U.S. 61/229,990; U.S. 61/229,996; U.S. 61/230,000; and U.S. 61/230,004.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care article in the form of a porous dissolvable solid structure, comprising:
   (a) from about 0% to about 75% surfactant;
   (b) from about 15% to about 70% polymeric structurant, wherein said polymeric structurant has a weighted average molecular weight of from about 40,000 to about 500,000; and
   (c) from about 1% to about 30% plasticizer;
   wherein the article is an open celled foam with a % open cell of from about 80% to about 100% and, wherein the article has a top and a bottom, and wherein the top comprises a concave acquisition region wherein the pores have an average diameter of from about 0.125 to about 0.850 mm and wherein the bottom has pores having an average diameter of from about 0.020 to about 0.125 mm.

2. The personal care article of claim 1, wherein the article comprises from about 23% to about 75% by weight of the article of surfactant.

3. The personal care article of claim 1, wherein the article comprises from about 30% to about 70% by weight of the article of surfactant.

4. The personal care article of claim 1, wherein the article comprises from about 40% to about 65% by weight of the article of surfactant.

5. The personal care article of claim 1, wherein the article has a design located at the acquisition region.

6. The personal care article of claim 1, wherein the top of the article comprise a design.

7. The personal care article of claim 1, wherein the bottom of the article has a convex region.

8. The personal care article of claim 1, wherein the article includes an indicia of orientation of top and bottom of the article.

9. The personal care article of claim 8, wherein the indicia is printed on the top of the article.

10. The personal care article of claim 8, wherein the indicia is molded on the article.

11. The personal care article of claim 1, wherein the top of the article and the bottom of the article are different colors.

12. The personal care article of claim 1, wherein the top of the article and the bottom of the article are different textures.

13. A personal care article in the form of a porous dissolvable solid structure, comprising:
   (a) from about 0% to about 75% surfactant;
   (b) from about 15% to about 70% polymeric structurant, wherein said polymeric structurant has a weighted average molecular weight of from about 40,000 to about 500,000; and
   (c) from about 1% to about 30% plasticizer;
   wherein the article is an open celled foam with a % open cell of from about 80% to about 100% and, wherein the article has a top and a bottom, and wherein the top comprises an acquisition region wherein the pores have an average diameter of from about 0.125 to about 0.850 mm and wherein the article has a concave area located at the acquisition region.

14. The personal care article of claim 11, wherein the article has a center and an edge, and the center thickness is less than the edge thickness.

* * * * *